(12) United States Patent
Wu et al.

(10) Patent No.: US 10,944,261 B2
(45) Date of Patent: *Mar. 9, 2021

(54) SURGICAL ROBOTIC ARM WITH WIRELESS POWER SUPPLY INTERFACE

(71) Applicant: Verb Surgical Inc., Mountain View, CA (US)

(72) Inventors: Qiong Wu, San Jose, CA (US); Koray Sahin, Mountain View, CA (US); Jonathan Bernard, Santa Clara, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 16/418,722

(22) Filed: May 21, 2019

(65) Prior Publication Data

US 2019/0372341 A1 Dec. 5, 2019

Related U.S. Application Data

(63) Continuation of application No. 15/959,143, filed on Apr. 20, 2018, now Pat. No. 10,333,296.

(51) Int. Cl.
*A61B 34/30* (2016.01)
*H02J 1/00* (2006.01)
(Continued)

(52) U.S. Cl.
CPC ............ *H02J 1/00* (2013.01); *A61B 34/30* (2016.02); *H01F 38/14* (2013.01); *H02J 50/12* (2016.02);
(Continued)

(58) Field of Classification Search
CPC ... H02J 1/00; H02J 50/90; H02J 50/12; H01F 38/14; A61B 34/30; A61B 2017/00221; A61B 2017/00477; A61B 2018/00178
See application file for complete search history.

(56) References Cited

U.S. PATENT DOCUMENTS

| 2012/0139355 A1* | 6/2012 | Ganem | H03H 7/40 307/104 |
| 2019/0051409 A1* | 2/2019 | Petrossian | A61B 5/0035 |

OTHER PUBLICATIONS

International Preliminary Report on Patentability for International Application No. PCT/US2018/030867 dated Oct. 29, 2020, 10 pages.

* cited by examiner

*Primary Examiner* — Daniel J Cavallari
(74) *Attorney, Agent, or Firm* — Womble Bond Dickinson (US) LLP

(57) ABSTRACT

A proximal end portion of a robotic surgical arm is to be coupled to an adapter of a surgical robotic platform, for use during a surgical session at the platform, and then decoupled from the adapter for storage until being re-coupled for use during another surgical session at the platform. A resonant-mode transformer-coupled power converter is provided that has a secondary side and a primary side. The secondary side is in the arm and has a transformer secondary coil in the proximal end portion of the arm. The primary side has a transformer primary coil in the adapter. The primary and secondary coils are held at positions and orientations that enable mutual inductive coupling between them for operation of the power converter when the arm is coupled to the adapter. Other embodiments are also described and claimed.

16 Claims, 5 Drawing Sheets

(51) Int. Cl.
 H02J 50/90 (2016.01)
 H02J 50/12 (2016.01)
 H01F 38/14 (2006.01)
 *A61B 17/00* (2006.01)
(52) U.S. Cl.
 CPC ..... H02J 50/90 (2016.02); *A61B 2017/00221* (2013.01)

SURGICAL ROBOTIC ARM WITH WIRELESS POWER SUPPLY INTERFACE

FIELD

An embodiment of the invention relates to power supplies for surgical robotic arms. Other embodiments are also described.

BACKGROUND

In a surgical robotic system, a robotic arm that has a surgical tool attached to it its distal end is remotely operated by a surgeon. Applications include endoscopic surgery, which involves looking into a patient's body and performing surgery inside, for example the abdominal cavity, using endoscopes and other surgical tools that are attached to the ends of several robotic arms. The system gives the surgeon a close-up view of the surgery site, and also lets the surgeon operate the tool that is attached to the arm, all in real-time. The tool may be a gripper with jaws, a cutter, a video camera, or an energy emitter such as a laser used for coagulation. The tool is thus controlled in a precise manner with high dexterity in accordance with the surgeon manipulating a handheld controller.

In a typical surgical robotic session, there may be up to five arms that need to be ready for being deployed at a surgical robotic platform, such as a table or bed on which the patient is resting. Installed within each arm is a communications interface for receiving robotic commands from, and providing for example video data to, a computerized, surgical console at which the surgeon sits while viewing a display screen that shows the surgical site and while manipulating the hand controller. Also installed within each arm is arm joint driver and control circuitry, and tool driver and control circuitry; the arm joint driver and control circuitry can drive several motorized joints (actuators) to pivot or translate various links of the arm so that the distal end of the arm is moved to a desired position as dictated by a user command; the tool driver and control circuitry can drive for example a gripper or cutter actuator or an energy emitter in the surgical tool (as dictated by a user command.) Electrical power that supplies the communications interface and the arm joint and tool driver and control circuitry may be delivered to the arm, via a power cable that is separate from the arm but connected to the arm at one end and to the surgical robotic platform at another end (e.g., to a power supply at the surgical table.) Alternatively, power may delivered to the arm through the use of pogo pins that come into electrical contact at a physical interface between the arm and an arm adapter at the robotic platform, when the arm is attached to the arm adapter.

SUMMARY

An embodiment of the invention is a surgical robotic arm having a wireless power supply interface to a surgical robotic platform. The arm has a proximal end portion and a distal end portion. The distal end portion is configured to receive a surgical tool. The proximal end portion is coupled to the surgical robotic platform, for example to an adapter of a surgical table on which a patient lies. The adapter adapts the surgical table to be coupled to the arm, so that the arm can be used for performing a surgery on the patient (while the patient is lying on the surgical table.) In one embodiment, the functions of the adapter may be viewed as being provided by the platform. The arm may have several linkages and actuated (motorized) joints in between adjacent linkages. The linkages can thus be rotated about a pivot axis at each joint, or can otherwise move, when power is supplied to arm joint driver circuitry that drives the actuators. The proximal end portion of the arm is also configured for being decoupled from the adapter, for storage of the arm until it is to be re-coupled for use during another surgical session at the platform.

To achieve wireless or contactless electrical power transfer between the surgical robotic platform and an electrical load in the arm, a resonant-mode transformer-coupled power converter is provided. The power converter has a primary side and a secondary side, where the primary side has a transformer primary coil that is in the adapter (of the platform), while the secondary side has a transformer secondary coil that is in the proximal end portion of the arm. Once the arm is coupled to the adapter, the primary and secondary coils are held at relative positions and orientations that enable mutual inductive coupling between them, for proper operation of the power converter which delivers the full power needed by the electrical load during the surgery. This avoids the need for pogo pins or separate power cables and power connectors, to deliver sufficient and reliable electrical power from the platform to the electrical load that is in the arm. This solution is especially desirable since the arm has to not only be coupled to the adapter, but then decoupled for storage once the surgery is over, and then recoupled to the adapter for another surgery, where this cycle repeats quite often (e.g., more than a handful of surgical sessions in a single day): the wireless power supply interface may be more reliable in the long term than electrical contact-based connectors or pogo pins which can degrade over time particularly at high current levels and are difficult to keep clean. Also, the no-contact wireless power supply interface may be washable in the operating room, another important convenience. The solution is also especially advantageous as there are several such arms that are coupled to the robotic platform and are needed for simultaneous operation during the surgery.

In one embodiment, the adapter at the robotic platform and the proximal end portion of the arm are configured so that the primary and secondary coils are fixed in position relative to each other once the arm has been coupled to the adapter, and remain in the same relative position while the arm is then used during a surgery.

In one embodiment, the adapter may have a pivot joint. A mechanical latching mechanism is provided that latches the arm to the pivot joint in the adapter, in a detachable and re-attachable manner. The pivot joint in the adapter enables the arm to rotate about a pivot axis of the joint. In that case, the secondary coil and the primary coil remain fixed in position relative to each other but move as one with the arm as the arm rotates around the pivot joint of the adapter.

As mentioned above, an electrical load in the arm is coupled to the output of the secondary side of the power converter. The load may include a communications interface and motor and energy emitter driver circuitry, where the latter drives several actuators (at multiple joints including one or more at the surgical tool) and, if attached, an energy emitting surgical tool. The driving is in accordance with several arm linkage joint control signals and one or more tool control signals, that are received by the communications interface, for example from a control tower. The control tower may have translated user commands received from a surgical console (signals that are sensing the orientation or position of a handheld controller), and based on robotic feedback information from the arm (e.g., accelerometer output data, thermal sensor output data, etc.) into robotic commands (arm linkage joint control signals in the arm's joint space, and one or more tool control signals) for the arm.

In one embodiment, the actuator control signals as well as any other control signals that are not part of the wireless electrical power delivery interface to the arm (which may be a resonant mode transformer coupled power converter as described above) are received and transmitted by the communications interface through a communications cable that may run from the arm to the control tower 3. Such a communications cable is thus in addition to the wireless power delivery interface, at each arm. The communications interface may also give robotic status feedback to generate the next command, and other status such as power consumption, temperature from a sensor in the arm or in the tool, and position from an accelerometer in the arm or in the tool.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

Figure 1:
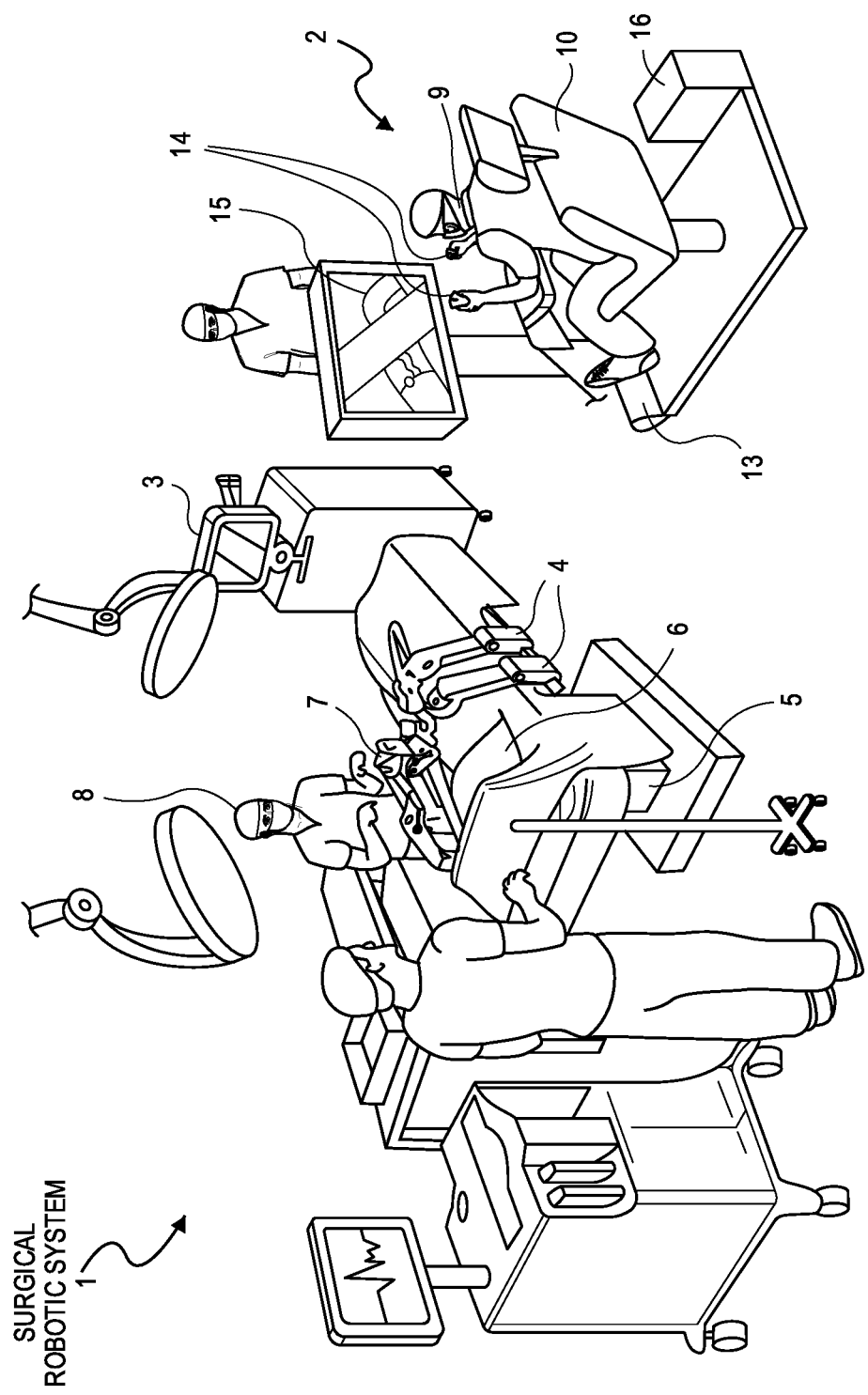
FIG. 1 is a pictorial view of an example surgical robotic system in an operating arena.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves another linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2A:
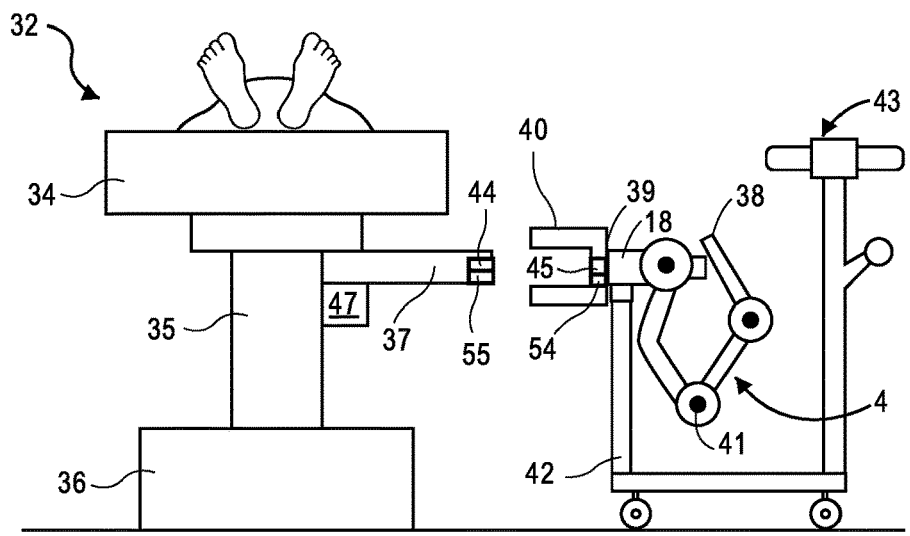
FIG. 2A shows an embodiment of a robotic surgical arm that is uncoupled from an example surgical robotic platform.

A surgical robotic apparatus that has a wireless power supply interface is now described. Referring to FIG. 2A, an example of a robotic surgical arm 4 is shown that is supported by a wheeled cart 43 and is ready to be coupled to the surgical robotic platform 5 for use during surgery upon the patient 6. Here, a human patient is shown as an example, lying flat on the upper face of a surgical tabletop 34. In this example, the surgical robotic platform 5 includes a surgical table 32 composed of the tabletop 34 on which the patient is lying on, and a table support 35 such as a pedestal that has raised the tabletop 34 above a floor and is stabilized by a table base 36 that is on the floor. The table support 35 may allow the tabletop 34 to have adjustable height, pitch, yaw or roll so as to enable a user such as a surgeon or assistant surgeon or nurse to perform a surgical procedure upon the patient 6 at a desired orientation or position. The table support 35 may also enable the tabletop 34 to be adjustable horizontally, either in a length direction of the tabletop or in a width direction.

The robotic arm 4 has a proximal end portion 39 and a distal end portion 38, between which are two or more (in the example shown here, three) arm joints 41. Each joint 41 is coupled to an adjacent pair of linkages. In the example shown, the arm 4 has three linkages but in general there may be more. The joints are motorized to enable precise and dexterous positioning of the distal end portion 38 to which a surgical tool 7 is attached, so that the distal end of the tool 7 can be precisely positioned inside the patient 6 during surgery. The linkage at the distal end portion 8 is configured to receive any one of several types of surgical tools 7 (not shown) such as any one of those mentioned earlier in connection with FIG. 1.

The robotic surgical arm 4 also has its proximal end portion 39 that is configured, by virtue of its coupling member 40, to be coupled to an adapter 37 of the surgical robotic platform 5, for use during a particular surgery session at the platform 5. In the example shown, the adapter 37 is secured to a surgical table 32. In other surgical platforms 5 however, the adapter 37 may be attached to for example a cart, a ceiling, a sidewall, or even another suitable support structure.

Figure 2B:
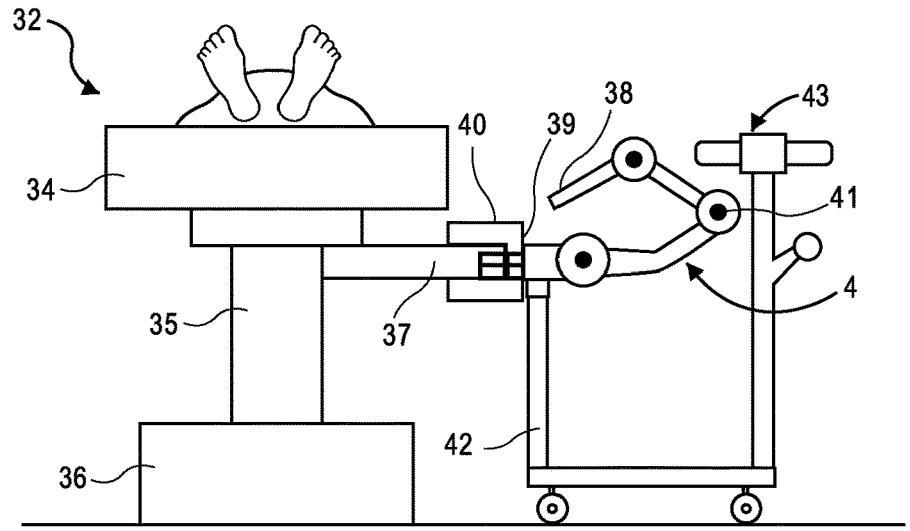
FIG. 2B shows the arm in its coupled state.

There may be several adapters 37 coupled to (or part of) the surgical robotic platform 5, where each is to receive a respective arm 4, but in the interest of conciseness FIG. 2A shows only one coupled to the surgical table 32. Each adapter 37 has a mechanical latching mechanism that latches the coupling member 40 of the arm 4 to the adapter 37, in a secure but detachable and re-attachable manner. The latching mechanism may be manually (human user) actuated by a lever or other hand-operated feature, or it may be motorized and automatically controlled to latch itself once the coupling member 40 of the arm 4 has been placed into position in a complementary part of the latching mechanism, as seen in FIG. 2B for example. The adapter 37 may be a rigid structural support member that mechanically engages with the coupling member 40 at the proximal end portion 39 of the arm 4, so as to securely affix the proximal end portion of the arm 4 to the robotic platform 5 in what is referred to here as its coupled state (during the surgical operation.) In the example shown, the adapter 37 is anchored to the tabletop support 35, and extends laterally or horizontally outward from the tabletop support 35. The adapter 37 may be affixed to the tabletop support 35 so as to move as one with the former, as the position and orientation of the tabletop 34 is adjusted. Alternatively, the adapter 37 may be affixed directly to the bottom or side of the tabletop 34, or directly to the floor through a separate support member (that is separate from the tabletop support 35 and that may also be adjustable in position (height) or orientation.)

Figure 2C:
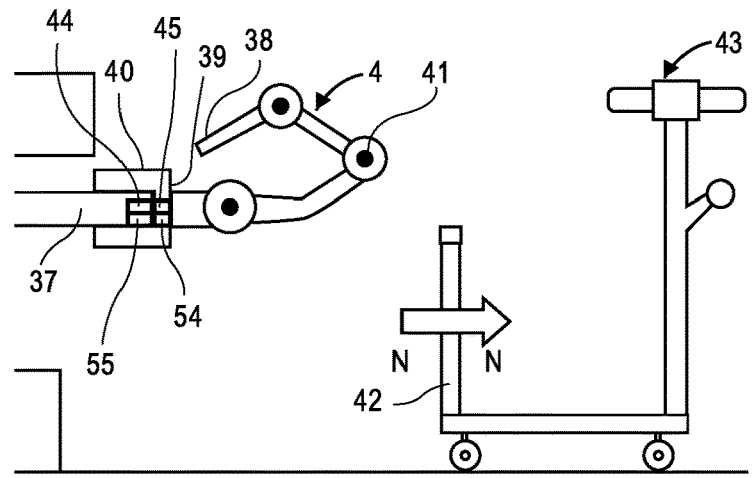
FIG. 2C shows the arm in its coupled state and ready to be used in the surgical operation.

In the robotic surgery arm 4, the coupling member 40 is designed so that it can be de-coupled from the adapter 37 once the surgery session has ended, so that the arm 4 can then be stored (e.g., on the cart 43), until the arm 4 is to be re-coupled to the adapter 37 for use during another surgical session at the platform. To illustrate this, FIG. 2A shows how the height of a support member 42 of the cart 43 has been adjusted so that a mouth of the coupling member 40 is brought to the same height as the adapter 37. Next, the cart 43 is wheeled towards the surgical table 32 until the mouth of the coupling member 40 engages the outside end of the adapter 37, and is then locked into that coupled position by the latching mechanism—see FIG. 2B. The cart 43 is then wheeled away from the surgical table 32 thereby leaving behind the coupled arm 4, as seen in FIG. 2C. The arm 4 is now ready for use in the surgical operation. This procedure may be repeated to bring a total of two, three or more arms into their coupled states at the surgical table 32, where each arm is locked into a fixed position at its respective adapter 37.

It should be noted that while the figures illustrate the example where the coupling member 40 of the arm 4 is a receptacle that receives and holds a "male" outside end of the adapter 37, an alternative is that the outside end of the adapter 37 is configured as a receptacle that receives and holds a male coupling member 40.

In another embodiment of the invention, the adapter 37 can pivot around a pivot joint (not shown), such that once the arm 4 is in its coupled state, it too will pivot about the pivot joint. The mechanical latching mechanism in that case may latch the coupling member 40 of the arm 4 to a complementary part of the adapter 37 that also pivots. The pivot axis may, for example, be a vertical axis. The mechanical latching mechanism for this embodiment may also be configured to detach and re-attach the arm 4, by for example being manually (human user) actuated by a lever or other hand-operated feature, or it may be motorized and automatically controlled to latch itself once the proximal end of the arm has been placed into position (at a complementary part of the latching mechanism that is on the pivot joint.)

Figure 4A:
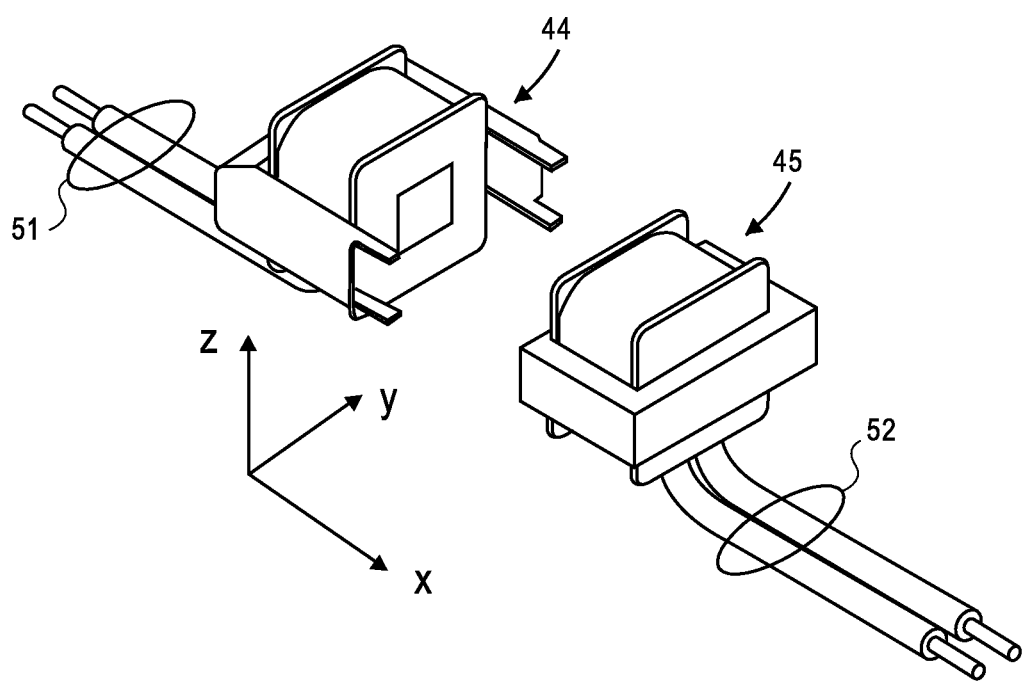
FIG. 4A is a perspective view of two parts of a multi-part transformer that may be used in the power converter.

Still referring to FIGS. 2A-2C, these figures also illustrate how wireless power transfer can be achieved, from the surgical robotic platform 5 to the electrical load in the arm 4, using a resonant mode transformer coupled power converter. The power converter may have a primary side 47 at the surgical platform 5, e.g., attached to the surgical table 32 as shown, that is coupled via mutual inductance to a secondary side 48 that is in the arm 4. The primary side 47 feeds power to a transformer primary part 44 that is in the adapter 37, while a transformer secondary part 45 that is in the arm 4 receives that power and feeds it to the secondary side 48. Examples of the transformer primary and secondary parts are shown in FIG. 4A and in FIG. 4B to be discussed below.

More generally, the transformer primary part 44 has a transformer primary coil or multi-turn winding that may be housed in the adapter 37, and the transformer secondary part 45 has a transformer secondary coil or multi-turn winding that may be housed in the proximal end portion 39 of the arm, and more specifically in the coupling member 40. The primary and secondary coils, or the primary part 44 and the secondary part 45, may be rigidly held at fixed positions and orientations relative to each other (once the arm 4 is coupled to the adapter 37 as seen for example in FIG. 2B and in FIG. 2C) that enable mutual inductive coupling between them for operation of the power converter.

As mentioned above, the electrical load in the arm 4 is powered by the output of the secondary side 48 of the power converter. The load may include a communications interface (communications circuitry), arm joint motor driver and control circuitry including arm joint brake driver and control circuitry (e.g., including brushless dc motor controllers), digital camera electronics, and energy emitter driver circuitry. The communications interface may be, for example, a serial peripheral interface bus, SPI, or other reliable digital communications interface that can deliver the arm linkage joint control and tool control signals from a computer system at the surgical platform 5, e.g., the control tower 3. The control tower 3 may have translated user commands received from the surgical console 2 (signals that are sensing the orientation or position of a handheld controller) and robotic feedback signals from the arm, into robotic commands, which may be the arm linkage joint control signals in the arm's joint space, and one or more tool control signals for the arm.

The arm joint motor driver and control circuitry drives or energizes several actuators (at multiple joints) in accordance with several arm linkage joint control signals that are received from the robotic surgical platform 5 (e.g., from the control tower 3—see FIG. 1), by the communications interface. The digital camera electronics forms part of a digital camera in the surgical tool 7, e.g., an endoscopic camera. The energy emitter driver circuitry serves to energize one or more energy emitters that are in the surgical tool 7, such as a coagulation laser or an ultrasonic emitter. In one embodiment, the actuator control signals as well as any other control signals that are not part of the wireless electrical power delivery interface to the arm 4 (which may include a resonant mode transformer coupled power converter as described above) are received and transmitted by the communications interface through a communications cable that may run from the arm 4 to the robotic surgical platform 5, e.g., to the surgical table 32 and then to the control tower 3.

Figure 3:
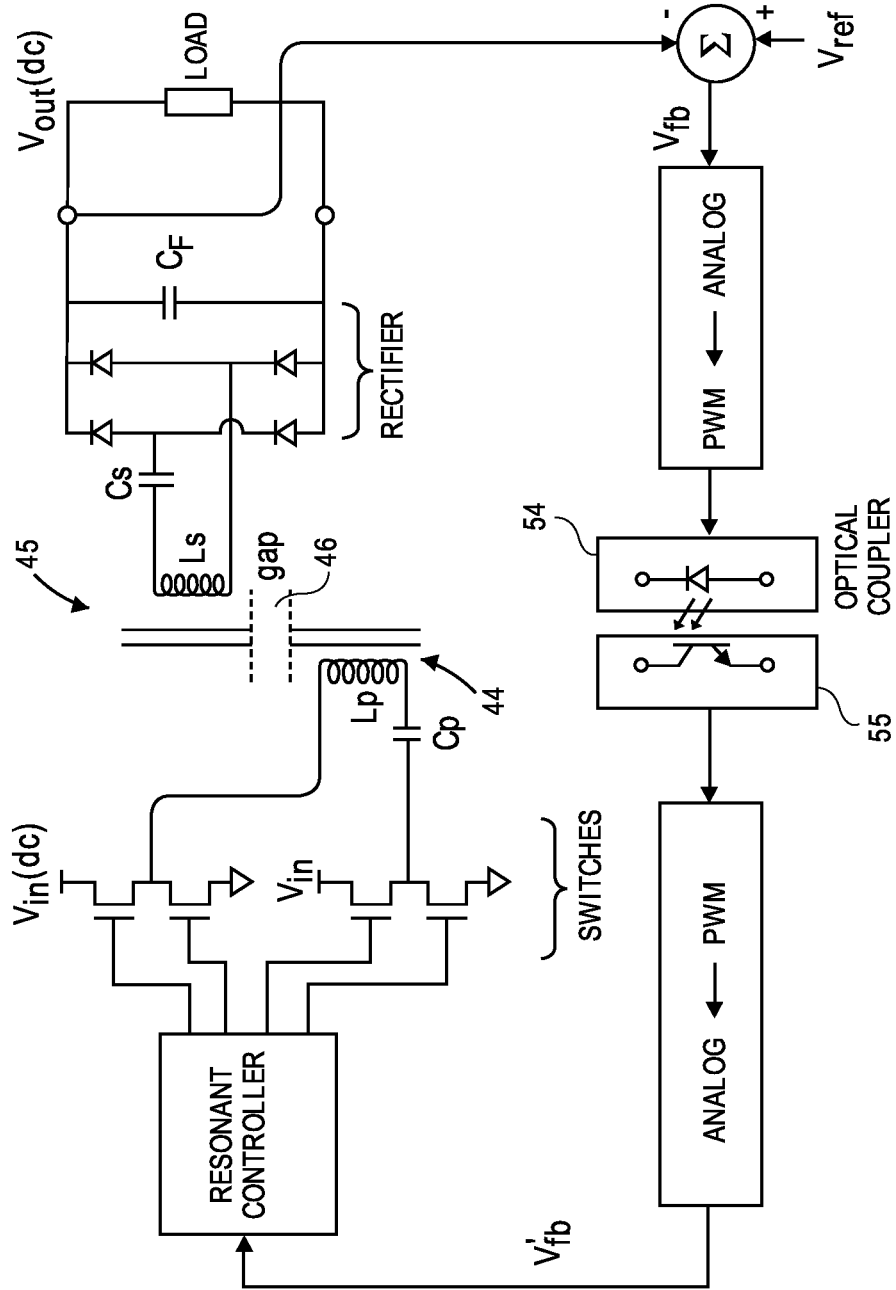
FIG. 3 is a circuit schematic of an example resonant mode transformer coupled power converter that enables wireless power transfer to the robotic surgical arm.

FIG. 3 shows a circuit schematic of an example of the resonant mode transformer coupled power converter. The primary side 47 of the power converter has a group of solid state switches (depicted in the example here as metal oxide semiconductor field effect transistors) that route power from a dc voltage rail at Vin(dc). The primary side 47 be housed in the adapter 37 as shown in FIG. 2A, but it could alternatively be housed in the tabletop support 35, in the base 36, or elsewhere on the surgical table 32 or even in another element of the robotic surgical platform 5. The dc voltage rail at Vin(dc) may be produced by a platform power supply (not shown), such as an ac-dc power converter that converts 120 Vac/240 Vac "wall power" that may be available in the operating room, to a suitable dc voltage. The platform power supply supplies the power that is drawn by the resonant mode power converter, which is in turn supplying the power that is drawn by the electrical load in the coupled arm 4. In other words, the output Vout(dc) of the resonant mode power converter is a power supply to the communications interface circuitry and the arm joint and tool driver circuitry in the arm 4, as described above. Just as an example, Vout(dc) may be 48 Vdc at 200 Watts.

The switches in the primary side 47 route power from Vin(dc) to feed a transformer primary coil Lp. The latter is part of a primary side resonant circuit, which is formed together with a capacitor Cp in the primary side 47. The switches are turned on and turned off under control of a switch mode power supply resonant controller also in the primary side 47, e.g., a transformer driver that drives the primary side resonant circuit with a 50% duty cycle square wave having a controlled working (switching) frequency, in order to transfer power to the secondary side 48 in a controlled, efficient manner, as needed by the electrical load in the arm 4 that is coupled to the output of the secondary side 48 at Vout(dc). The secondary side 48 has a transformer secondary coil Ls, which is part of a secondary side resonant circuit along with capacitor Cs. There is mutual inductive coupling of magnetic flux across a non-conductive (electrically insulating) gap 46 between the coils, from the transformer primary part 44 to the transformer secondary part 45. This enables switch mode power transfer from the primary side 47 to the secondary side 48. The power required by the load may be met by changing the switching frequency of the control signal of the resonant controller in the primary side 47, e.g., by matching the switching frequency with the resonance frequency of the L-C based resonant circuit in the primary side in order to increase power transfer. The closer the switching frequency to the resonant frequency (fr) of Lp and Cp, the higher the voltage at the secondary side 48. When Vout is lower than the setting voltage, which may be for example 48V, the feedback signals make the controller switching frequency closer to the resonant frequency (fr) to make Vout higher. When Vout great than the setting voltage, the feedback signal can force the switching frequency away from fr to make Vout lower. The feedback signal is an analog signal, e.g., Vfb, and as explained below may be converted into a PWM waveform before being passed over an optical interface over the gap, or alternatively by the communication interface circuitry mentioned above. Note that the turns ratio of the primary coil to the secondary coil need not be 1:1.

The ac (switched) voltage at the output of the resonant circuit Ls-Cs is converted into dc by a rectifier (in this example, a full wave rectifier composed of the four diodes as shown) and then filtered by a filter capacitor Cf, resulting in the output voltage Vout(dc). If regulation of Vout(dc) is desired, then this may be achieved by configuring the resonant controller to vary the switching frequency of its control of the switches, in a feedback controlled manner. This would be in response to a feedback voltage Vfb that represents an error or difference between a reference voltage Vref and the power converter output voltage Vout(dc). The feedback voltage Vfb may be provided to the resonant controller, not in its original form but rather in the form of Vfb', where Vfb is converted in the secondary side 48 into a PWM signal, before it is then transmitted by an optical transmitter 54 of an optical coupler to an optical receiver 55 in the primary side 47, where it is then converted back into analog form as Vfb' before being used by the resonant controller. The technique of converting the feedback signal into digital form (e.g., as a PWM signal) for its transfer from the arm 4 to the robotic surgical platform 5 increases immunity to noise during the transfer. Other techniques for delivering the feedback voltage Vfb from the secondary side 48 to the primary side 47 in a wireless or contact-less manner across the electrically insulating gap 46 include the use of an auxiliary transformer. In yet another embodiment, the feedback voltage Vfb' is received in the primary side 47 via a cabled communications interface with the secondary side 48 in the arm 4, e.g., the same SPI that is used by the communications interface in the arm 4 for receiving the robotic commands from the control tower 3.

Figure 4B:
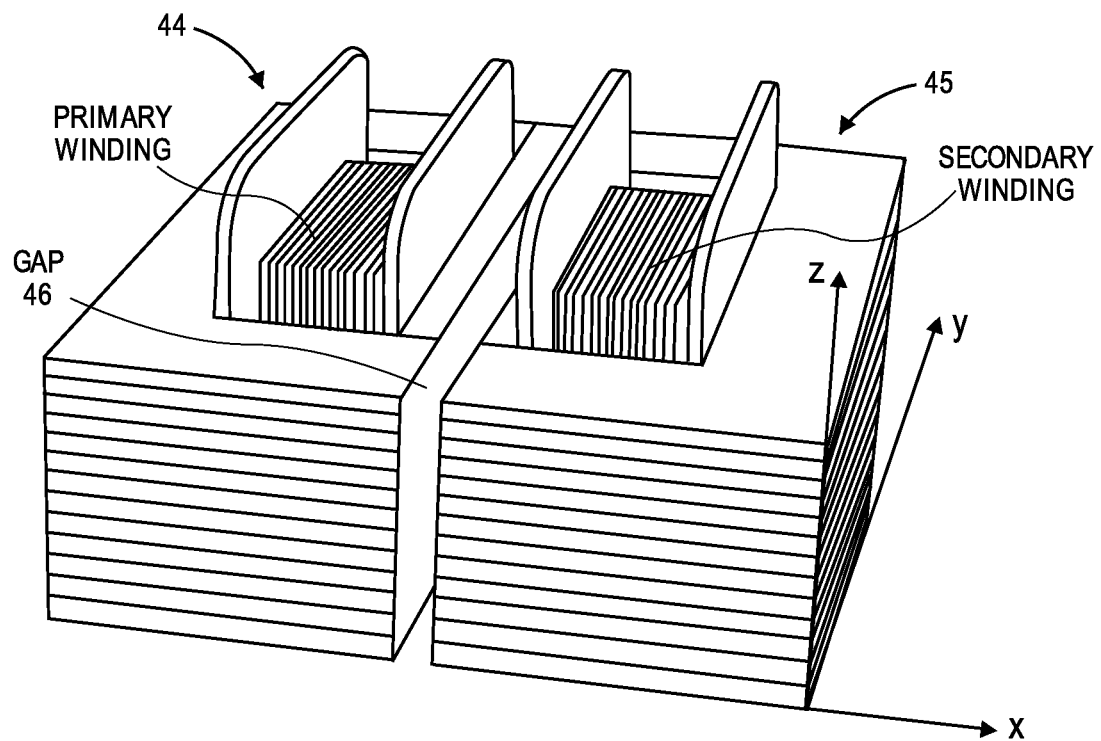
FIG. 4B is a perspective view of the multi-part transformer in the coupled state, where the constituent parts have been brought adjacent to each other to enable mutual inductance coupling between the primary and secondary coils.

FIG. 4A and FIG. 4B are perspective views of the two parts of an example multi-part transformer, that may be used in the resonant mode transformer coupled power converter of FIG. 3. The transformer primary part 44, which is in the proximal coupling member 40 of the arm 4 (see FIGS. 2A-2C), and has a primary coil that terminates in a pair of primary terminals 51. There is also the transformer secondary part 45, which is in the adapter 37 and has a secondary coil that terminates in a pair of secondary terminals 52. FIG. 4A shows the transformer in its un-coupled state, when the arm 4 has been de-coupled from the adapter 37 for purposes of storage—see FIG. 2A: the primary part 44 is spaced so far apart from the secondary part 45 that there is insufficient mutual inductive coupling between them (to transfer enough power to supply the electrical load in the arm 4.) In contrast, FIG. 4B shows the transformer in its coupled state, when the arm 4 is coupled to the adapter 37—see FIG. 2C. There, the primary part 44 has been brought close enough to the secondary part 45 such that the two are separated only by the gap 46—see FIG. 3. This state allows sufficient power to be transferred from the primary to the secondary (so as to supply the electrical load in the arm 4.)

In the particular example of FIG. 4A and FIG. 4B, the multi-part transformer may have a core form or a shell form in which each of the primary coil and the secondary coil is wound around a respective, magnetic or ferromagnetic core or shell portion that may be composed of laminated steel (steel sheets lying in the x-y plane and stacked in the z-direction.) As seen in the figures, in each of the primary part 44 and the secondary part 45 of the transformer, there is a pair of support plates that support the coil of that part, one on the left side and another on the right side of the coil. The four support plates are all parallel to each other, and the two inner ones may be separated by less than 5 mm once the arm 4 has been coupled to the adapter 37 (resulting in the coupled state shown in FIG. 4B.) For each of the primary part 44 and the secondary part 45 of the transformer, the core form or shell form part may be composed of magnetic or ferromagnetic material such as laminated steel.

The transformer primary part 44, including the primary coil, may be entirely encapsulated by insulating material, as is the secondary part 45. This may ensure that the coils are not exposed to touch, which is particularly desired when the coils support peak to peak voltages that are greater than 60 Vac. The encapsulation material may be selected to have sufficient magnetic permeability, e.g., containing ferrite particles, and it may fill the entire gap 46 as seen in FIG. 4B, where the flat outside face of the encapsulated primary part 44 will abut the flat outside face of the encapsulated secondary part 45 (so as to enable efficient mutual inductive coupling between the primary coil and the secondary coil at the switching frequency of the power converter.)

As seen in the figures, each part of the multi-part transformer may have a flat face that becomes aligned with, and is held at a fixed distance from, the other part of the multi-part transformer, when the arm 4 has been coupled to the adapter 37. Note that perfect alignment in the x, y and z-axes that are shown is not necessary during working or operation of the arm 4. However, misalignment in any of the axes may result in a reduction in efficiency of the power transfer. In one embodiment, once the arm 4 is coupled to the adapter 37, there may be an electrically insulating gap 46 of no more than 5 mm between the primary coil and the secondary coil, which may ensure sufficient mutual inductive coupling to deliver at Vout(dc), 200 W at 48V. In one embodiment, the flat outside faces of the encapsulated primary and second parts abut each other, while maintaining the gap 46 between the primary and secondary coils.

In the example of FIGS. 2A-2B, the primary and secondary coils are positioned such that the mutual inductive coupling (magnetic flux) between them is through the lateral or side faces of their respective "housings", which are the adapter 37 and the coupling member 40, respectively. They could however be positioned differently. For example, the primary and secondary coils could be positioned such that the mutual inductive coupling is through the top face of the adapter 37 and the inner top face of the coupling member 40, at the interface or boundary between the two housings. In another example, the primary and secondary coils could be positioned so that the mutual inductive coupling is through the bottom face of the adapter 37 and the inner bottom face of the coupling member 40.

In the example of FIGS. 2A-2B, the lateral or side faces of the two housings of the adapter 37 and the coupling member 40 define a vertical interface or boundary, through which the magnetic flux lines of the mutual inductive coupling pass from one housing to the other. This suggests that the primary and secondary coils could have the same orientation, e.g., the length axes of both may be vertical, as seen in FIG. 4B. But their orientation may be different such that the interface or boundary between them need not be vertical. For example, the two coils could be tilted in the same direction, such that the magnetic flux lines of their mutual inductive coupling cuts through a diagonal boundary line (rather than a vertical boundary as seen in FIG. 4B.) In other words, the primary and secondary coils may be oriented differently than shown in FIGS. 2A-2C and in FIG. 4B, so that the magnetic flux lines of their mutual inductive coupling cross an interface boundary that is not vertical.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while FIG. 3 depicts a resonant mode transformer coupled power converter having a particular arrangement of a full bridge switch circuit and a series resonant circuit in the primary side 47, and a series resonant circuit and a full wave diode-based rectifier in the secondary side 48, other arrangements for the switches and resonant circuits of the power converter are possible (e.g., a half bridge switch circuit, a parallel resonant circuit, a series-parallel resonant circuit, and an active rectifier.) The description is thus to be regarded as illustrative instead of limiting.

What is claimed is:

1. A surgical robotic apparatus comprising:
   a surgical robotic arm configured to be removably coupled to a surgical robotic platform for surgery and decoupled from the platform for storage; and
   a transformer secondary coil of a transformer-coupled power converter that also has a transformer primary coil,
   wherein the secondary coil is in the arm and the primary coil is in the platform and there is inductive coupling between the primary and secondary coils for operation of the power converter when the arm is coupled to the platform.

2. The apparatus of claim 1 wherein the arm comprises a coupling member formed as a receptacle to receive an adapter of the platform, wherein the coupling member has a mechanical latching mechanism that latches the coupling member to the adapter, in a detachable and re-attachable manner.

3. The apparatus of claim 1 wherein the arm comprises:
   a male coupling member that is to be received by an adapter of the platform, wherein the male coupling member has a mechanical latching mechanism that latches the male coupling member to the adapter, in a detachable and re-attachable manner.

4. The apparatus of claim 1 wherein the secondary coil and the primary coil are fixed in position relative to each other once the arm has been coupled to the adapter.

5. The apparatus of claim 4 wherein the secondary coil is part of a second part of a multi-part transformer that also has a first part, wherein the multi-part transformer is of a core form or a shell form in which each of the primary coil and the secondary coil is wound around a respective, magnetic or ferromagnetic core or shell portion, and wherein the second part of the multi-part transformer is in the arm while the first part is in the platform.

6. The apparatus of claim 5 wherein the first part of the multi-part transformer has a flat face that becomes aligned with, and is held at a fixed distance from the second part of the multi-part transformer when the arm has been coupled to the platform, and wherein in that position there is an electrically insulating gap between the primary coil and the secondary coil.

7. The apparatus of claim 1 wherein the primary and secondary coils are parts of a multi-part transformer, wherein the multi-part transformer is of a core form or a shell form in which each of the primary coil and the secondary coil is wound around a respective, magnetic or ferromagnetic core or shell portion, and wherein the part of the multi-part transformer that has the secondary coil is in the arm while the part that has the primary coil is in the platform.

8. The apparatus of claim 7 wherein the multi-part transformer comprises a first support plate that supports the primary coil, and a second support plate that supports the secondary coil, and wherein the first and second supports are parallel to each other and separated when the arm has been coupled to the platform.

9. The apparatus of claim 1 wherein the secondary coil is part of a second part of a multi-part magnetic transformer that also has a first part, wherein the multi-part magnetic transformer is of a coreless form, and wherein the second part of the multi-part transformer is in the arm while the first part is in the platform.

10. The apparatus of claim 1 further comprising an electrical load coupled to an output of the power converter, wherein the electrical load comprises:
    a communications interface in the arm, configured to receive an arm actuator control signal; and
    motor driver circuitry in the arm that is coupled to the communications interface and configured to be controlled by the arm actuator control signal.

11. The apparatus of claim 10 wherein the power converter comprises an optical coupler having a transmitter that is affixed to the arm and transmits a feedback signal derived from the output of the power converter, and wherein the optical coupler has a receiver that is affixed to the platform and receives the feedback signal when the arm is coupled to the platform.

12. The apparatus of claim 2 wherein the adapter comprises a pivot joint that enables the coupling member to rotate about a pivot axis of the joint.

13. The apparatus of claim 1 wherein the power converter comprises an optical coupler having a transmitter that is affixed to the arm and transmits a feedback signal derived from the output of the power converter, and wherein the optical coupler has a receiver that is affixed to the platform and receives the feedback signal when the arm is coupled to the platform.

14. The apparatus of claim 3 wherein the adapter comprises a pivot joint that enables the coupling member to rotate about a pivot axis of the joint.

15. A method for operating a surgical robotic apparatus, the method comprising:
    coupling a surgical robotic arm to a surgical robotic platform for surgery; and
    initiating wireless power delivery to the arm through a transformer secondary coil of a transformer-coupled power converter that also has a transformer primary coil, wherein the secondary coil is in the arm and the primary coil is in the platform and there is inductive coupling between the primary coil and the secondary coil for operation of the power converter when the arm is coupled to the platform.

16. The method of claim 15 further comprising
    decoupling the arm from the platform for storage of the arm.

* * * * *